United States Patent [19]

Wagner et al.

[11] Patent Number: 5,646,305

[45] Date of Patent: Jul. 8, 1997

[54] OXYGEN ENRICHMENT PROCESS FOR AIR BASED GAS PHASE OXIDATIONS WHICH USE METAL OXIDE REDOX CATALYSTS

[75] Inventors: Matthew Lincoln Wagner, White Plains, N.Y.; Donald Walter Welsh Kirkwood, Oakville, Canada; Kazuo Kiyonaga, Honolulu, Hi.

[73] Assignee: Praxair Technology, Inc., Danbury, Conn.

[21] Appl. No.: 579,109

[22] Filed: Dec. 27, 1995

[51] Int. Cl.[6] .................... C07D 307/60; C07B 33/00
[52] U.S. Cl. .................... 549/259; 549/256; 549/257; 549/248; 549/249; 558/319; 558/327; 562/544; 568/475; 568/476; 546/286
[58] Field of Search .................... 549/256, 257, 549/259, 248, 249; 558/319; 568/475

[56] References Cited

U.S. PATENT DOCUMENTS

| | | | |
|---|---|---|---|
| 4,668,802 | 5/1987 | Contractor | 549/259 |
| 5,132,482 | 7/1992 | Smith et al. | 585/500 |
| 5,466,857 | 11/1995 | Reiling et al. | 558/319 |

OTHER PUBLICATIONS

Xiaosu Lang et al, "Application of Periodic Operation to Maleic Anhydride Production", *The Canadian Journal of Chemical Engineering*, vol. 67, Aug. 1989, pp. 635–645.

E. Fiolitakis et al, "Investigation of the Catalytic Oxidation of Benzene to Maleic Anhydride by Wave Front Analysis with Respect to the Application of Periodic Operation" *The Canadian Journal of Chemical Engineering*, vol. 61, Oct. 1983, 703–709.

X.-S. Lang et al, "Selectivity Improvement Using Alternate Flushing and Reactant Cycle Steps", *The Canadian Journal of Chemical Engineering*, vol. 69, Oct. 1991.

Y.A. Saleh–Alhamed et al, "Periodic Operation Studies of the Partial Oxidation of Propylene to Acrolein and Acrylic Acid", *Chemical Engineering Science*, vol. 47, No. 9–11,. pp. 2885–2890, 1992.

Peter L. Silveston et al, "Influence of Composition Modulation on Product Yield and Selectivity in the Partial Oxidation of Propylene over an Antimony–Tin Oxide Catalyst", *Ind. Eng. Chem. Des. Dev.*, 1985, 24, pp. 320–325.

Rashmi Contractor et al, "Butane Oxidation in a Transport Bed Reactor–Redox Characteristics of the Vanadium Phosphorus Oxide Catalyst", *New Developments in Selective Oxidation 1990*, pp. 553–562.

P.H. Calderbank, "Kinetics and Yields in the Catalytic Oxidation of o–Xylene to Phthalic Anhydride with $V_2O_5$ Catalysts", *Chemical Reaction Engineering–II*, 646–653. (1974).

Fabrizlo Cavani et al, "Oxidation of 1–Butene and Butadiene to Maleic Anhydride. 1. Role of Oxygen Partial Pressure", *Ind. Eng. Chem. Prod. Res. Dev.*, 1983, 22, 565–570.

Frank–Dieter Kopinke et al., "New Developments In Selective Oxidation By Heterogeneous Catalysis", *Studies in Surface Science and Catalysis*, vol. 72 pp. 15–22 (1992).

R.M. Contractor et al, "Selective Oxidation in Riser Reactor", *Catalysis Today*, 3, (1988), 175–184.

*Primary Examiner*—Bernard Dentz
*Attorney, Agent, or Firm*—Robert J. Follett

[57] ABSTRACT

This invention is directed towards an improved process for the selective gas phase oxidation of a organic reactant using a metal oxide redox catalyst, wherein the organic reactant and air feeds are at a substantially continuous level, the improvement comprising adding a fluctuating flow of oxygen at alternating relatively high and relatively low levels. The invention also teaches means by which a gas may be provided to a reaction process on a fluctuating basis.

18 Claims, 7 Drawing Sheets

OXYGEN ENRICHMENT PROCESS FOR AIR BASED GAS PHASE OXIDATIONS WHICH USE METAL OXIDE REDOX CATALYSTS

FIELD OF THE INVENTION

This invention is directed towards the use of oxygen in air based gas phase oxidation reactions which use metal oxide redox catalysts. More particularly, the invention is directed towards providing oxygen to such reactions on a fluctuating basis, and means for accomplishing this.

BACKGROUND

Air based gas phase reactions which use metal oxide redox catalysts are used in chemical synthesis of acrylic acid, acrylonitrile, formaldehyde, maleic anhydride, acrolein, isophthalonitrile, nicotinonitrile and phthalic anhydride. A typical redox catalyst is vanadium-phosphorus, though others are well known in the art.

In the design of existing reactors both production and yield are taken into consideration. In this regard, it is recognized that there is a trade-off between production and yield such that parameters which provide a high level of production may, in fact, have the effect of decreasing product yield. For example, in order to increase production from an existing reactor, reactant feed rates must be increased; however, this has negative side-effects. Typically this procedure lowers the oxygen-to-feed ratio because air compressor and/or pressure drop limitations do not allow for an increase in the air flow rate.

Due to this lower oxygen-to-feed ratio, the partial pressure of oxygen in the reactor atmosphere may become insufficient to reoxidize the metal oxide catalyst which then becomes over-reduced and, eventually, deactivated. The net result is that product yields are depressed. Redox catalyst over-reduction also leads to a shortening of catalyst lifetime because the reduced form of these catalysts is relatively unstable.

The basic mechanism behind redox catalyst over-reduction can be understood by examining the following reactions which are applicable for any gas phase partial oxidations performed with metal oxide redox catalysts.

1) organic reactant+oxidized catalyst→product +reduced catalyst 2) reduced catalyst+oxygen→oxidized catalyst As can be seen above, as the organic reactant reacts, the catalyst is reduced (Reaction 1). In order for the catalyst to be returned to its active oxidized state, it must be re-oxidized by gas phase oxygen (Reaction 2). If one has too much organic reactant and not enough oxygen, as when there is a high reactant feed rate, too much catalyst remains in the reduced state, and the catalyst is considered over-reduced.

As indicated above an over-reduced catalyst will be deactivated relative to the oxidized state. This deactivation is due to a combination of the following effects: chemical transformation of an active component into a less active component; reduction of active catalyst surface area through particle sintering, and the volatilization and loss of an active component. These effects are generally related to the unstable nature of a reduced catalyst and result in depressed reaction yield (e.g. the amount of desired product produced) and catalyst lifetime.

Thus, typically, manufacturers have accepted either the lowering of yield and catalyst lifetime associated with operating with a low oxygen-to-feed ratio, or the reduction in production associated with operating with a high oxygen-to-feed ratio.

One solution to this problem has been to add a continuous flow of oxygen to the air entering a reactor in order to maintain the oxygen-to-feed ratio during periods of increased production. This "oxygen enrichment" improves the rate of reoxidation of the catalyst, ameliorates over-reduction and thus allows one to maintain product yield while increasing the reactant feed flow to the reactor. This use of oxygen enrichment is usually only applicable to fluid bed reactors because these reactors are typically able to handle the increased heat load brought about by the increased amount of reaction. In this process, oxygen is typically injected into the air feed line of a reactor.

Using oxygen enrichment in the manner described above is applicable only in a retrofit application when market conditions make increased production from an existing plant desirable. Typically, such increases in production will only be desired for a fraction of the plant's operating life. Unfortunately this creates an fluctuating demand for oxygen which is difficult and costly to supply.

For a fixed bed reactor, continuous oxygen enrichment can be employed to increase the oxygen-to-feed ratio at a fixed production level or feed flow rate. This oxygen enrichment improves the rate of reoxidation of the catalyst, ameliorates over-reduction and thus allows one to increase product yield while maintaining the reactant feed flow to the reactor. Unfortunately, continuous oxygen enrichment is generally not economical as the savings associated with the yield increase are not enough to pay for the additional oxygen required.

For fixed bed reactors, the amount of oxygen added is usually between 1 and 3 vol. % of the total volume of all gases in the reaction atmosphere, as above this level there is no longer an improvement in yield. By the term "reaction atmosphere" we mean the total amount of all gases entering the reactor. If this oxygen were added to the air stream, this addition would result in a total oxygen concentration of about 22–24 vol. % in the air stream, or 1–3 vol. % enrichment. By the terms "volume % enrichment" or "% enrichment" we mean the difference between the oxygen vol. % in air and the oxygen vol. % in the mixture that would result if all the oxygen were added to the air stream.

It should noted that the oxygen concentration in the total volume of all the gases in the reactor is slightly less when compared to the oxygen concentration in the air stream-oxygen mixture, because the amount of oxygen is diluted by gaseous organic reactant which is present in an amount between 1 vol. % and 2 vol. % in fixed beds. The dilution factor is much greater with fluidized bed reactors as the amount of gaseous organic reactant is much higher. For example, the entering feed concentration, which includes ammonia in ammoxidation reactions, ranges from 4 vol. % for maleic anhydride to approximately 17 vol. % for acrylonitrile.

Several laboratory experiments have been conducted with metal oxide systems that vary the oxygen-to-feed ratio by cycling the reactant feed flow (Saleh-Ahlamad, 1992; Fiolitakis, 1983; Silveston, 1985). The reactant feed flow is varied either by pulsing the reactant feed on and off or at relatively high and low levels. Some selectivity improvement (e.g. how much of actual reacted starting material produces the desired product) has been noted in these experiments. However, in all but one example (Saleh-Ahlamad, 1992) the yield is lowered because of the reduction in conversion (e.g. the amount of starting material that actually reacts). Moreover, reactant feed cycling forces periodic operation of the entire plant, which adds to the complexity of the plant, and may actually reduce the overall performance of the plant, since most process equipment is designed to operate continuously.

Other laboratory experiments have alternately exposed metal oxide catalysts to reactant feed and to oxygen (Lang, 1989; 1991). This, in effect, is reactant feed and oxygen cycling. Some of these experiments have also included periodic flows of nitrogen to flush the catalyst. As with the reactant feed cycling experiments, while some selectivity increase was noted, product yield decreased. Further, such cycling increases the complexity required for plant operation.

Contractor, in U.S. Pat. No. 4,668,802, teaches a transport bed process for maleic anhydride which circulates the catalyst from a reaction zone where it is contacted with butane, to a stripping zone where the maleic anhydride is removed from the catalyst, and to a regeneration zone wherein the catalyst is contacted with an oxygen containing gas mixture. The oxygen and butane are never mixed together, thus effectively creating an alternating flow of oxygen and reactant feed with respect to the catalyst. This process enables high selectivities to be obtained while keeping throughput high.

However, transport bed technology is complex to design and operate and is not retrofitable. It is also difficult to produce the required attrition resistant catalyst. Finally, due to backmixing within the bed, the process is limited to chemicals capable of being produced in fluid beds. To date, the process has been applied only to maleic anhydride production.

As can be seen from the above discussion, under current processes one must accept either lower yields, lower production, or increased capital costs.

OBJECTS OF THE INVENTION

It is therefore an object of the invention to provide an improved method for gas phase oxidations which use metal oxide redox catalysts.

It is a further object of the invention to provide a method which allows for both increased production and increased yield.

It is a still further object of the invention to provide a method for gas phase oxidations in which oxygen is provided in alternating relatively high and relatively low amounts such that the benefits of increased production, increased yield and longer catalyst life are realized and the cost of the additional oxygen required is offset.

It is another object of the invention to provide methods by which oxygen can be provided to the gas phase oxidation process of the invention.

SUMMARY OF THE INVENTION

This invention teaches an improved process for the selective gas phase oxidation of an organic reactant using a metal oxide redox catalyst, wherein the organic reactant and air feeds are at a substantially continuous level, the improvement comprising adding oxygen to the gas phase in alternating relatively high and relatively low amounts.

In a preferred embodiment the oxidation takes place in a fixed-bed reactor or a fluidized-bed reactor.

In other embodiments, the relatively low amount is preferably greater than or equal to 0% enrichment, more preferably 0% enrichment, and is less than the relatively high amount.

In still other embodiments, the relatively high amount of oxygen is preferably less than or equal to 9%, more preferably 1–3% enrichment, and is greater than the relatively low amount.

The invention also includes processes by which oxygen may be provided in relatively high and relatively low amounts to a reaction.

In preferred embodiments, these processes include the use of a manifold or a baffle in a fixed-bed reactor to provide oxygen to the catalyst containing tubes therein, on an individual or grouped basis.

In another preferred embodiment, oxygen is provided to various regions of either a fixed-bed or fluid-bed reactor through the use of injector ports located in these regions.

In another preferred embodiment, oxygen is provided through means of a single adsorption bed connected directly to the reaction.

In another preferred embodiment, a flow of oxygen is cycled between reactors in a multiple parallel reactor production system.

In still another preferred embodiment, an accumulator is provided between the oxygen source and the reactor such that while a continuous flow is provided to the accumulator, an alternating relatively high and relatively low flow is withdrawn and provided to the reactor.

BRIEF DESCRIPTION OF THE DRAWINGS

Other objects, features and advantages will occur to those skilled in the art from the following description of the preferred embodiments and accompanying drawings, in which.

DETAILED DESCRIPTION OF THE INVENTION

Our invention has been derived from observations associated with continuous oxygen enrichment processes in redox catalyst driven gas phase oxidations. While not wishing to be bound by any theory, the explanation below discloses what we believe to be the mechanism behind our invention.

Figure 1:
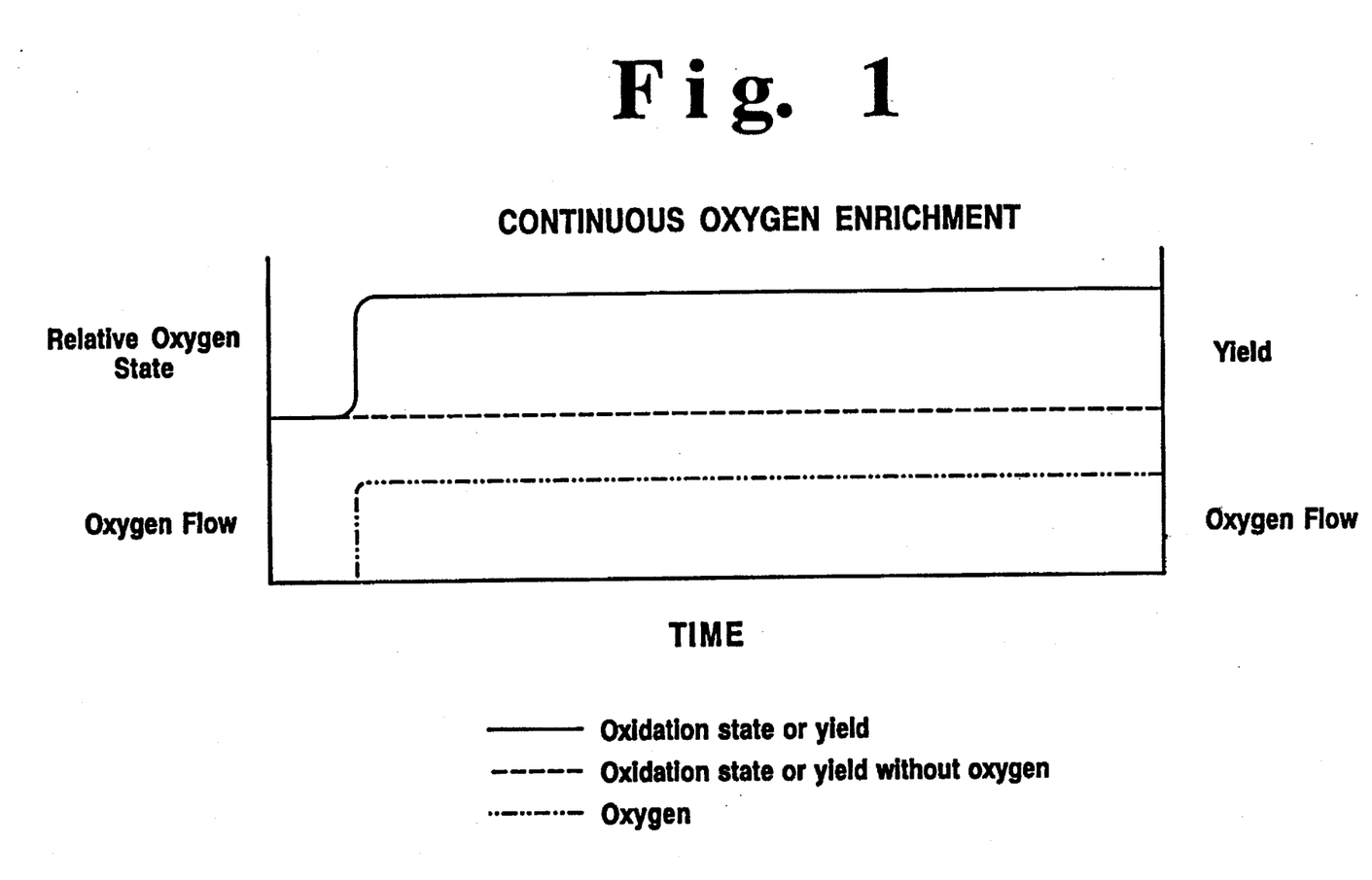
FIG. 1 is a graphical representation which shows a conventional enrichment process.

During reaction, the catalyst continuously undergoes reduction and oxidation. The rate of reduction and the rate of oxidation balance to produce a catalyst with a certain overall state of oxidation. When additional oxygen is added, the relative rates of oxidation and reduction change and a new equilibrium is obtained. If the catalyst is normally operated in an over-reduced state, this new balance is associated with a different overall state of oxidation. Since more oxygen has been added, this new state of oxidation will be a higher state than the previous one (if such a state is possible). This higher oxidation state roughly corresponds to an increase in yield, which like oxidation state, has a maximum value which may be achieved. This is graphically represented in FIG. 1, which shows oxidation state and yield for a continuous enrichment process.

Similarly, when the additional oxygen is withdrawn, the rates of oxidation and reduction will balance once again to produce the original state of oxidation. This state of oxidation is lower than that obtained with the additional oxygen. In each of the above cases, there is a finite time associated with the transition from the lower to higher and higher to lower oxidation states, respectively.

If operating without the addition of oxygen results in an over-reduced catalyst and operating with the additional oxygen ameliorates this over reduction, the transition from one oxidation state to another will be accompanied by variations in yield. If the time it takes to transform from the lower oxidation state to the higher oxidation state is smaller than the time to transform from the higher state to the lower, then one may use a fluctuating supply of oxygen to produce an average yield increase greater than that obtained if the same absolute amount of oxygen was added continuously.

In practice, we have observed in benzene-based maleic anhydride production that the yield increase associated with using continuous oxygen enrichment to increase the oxygen-to-feed ratio lingers for sometime after it was withdrawn. Additionally, no delay was noted for the onset of the yield increase. Thus, the transition from the over-reduced to the more oxidized state was very quick. Together, these observations suggest that for this system under these conditions, the transition from the higher to lower oxidation state upon removal of the additional oxygen takes longer than the transition from the lower oxidation state to the higher oxidation state.

The above observations support our conclusion that a relatively high average yield increase need not require that oxygen be provided in a continuous flow. Rather, the same advantage could be obtained for metal oxide redox systems by providing a fluctuating source of oxygen while maintaining a continuous air and reactant feed flow. This inventive process offers several advantages over conventional processes.

As compared to continuous oxygen enrichment, by using an oxygen on a fluctuating and/or intermittent basis, oxygen requirements are reduced and the economics of oxygen addition are improved.

In addition, providing oxygen on a fluctuating and/or intermittent basis is better than reactant feed cycling, alternating reactant feed and oxygen, and transport bed technologies not only because of increased yields, but also due to its ease of installation and operation. Finally, unlike reactant feed cycling and the alternating of oxygen and reactant feed, fluctuating and/or intermittent oxygen enrichment improves yield without sacrificing production.

Two preferred methods of the invention are disclosed below. These are meant to be illustrative, and are not intended to limit the scope of the invention.

Figure 2A:
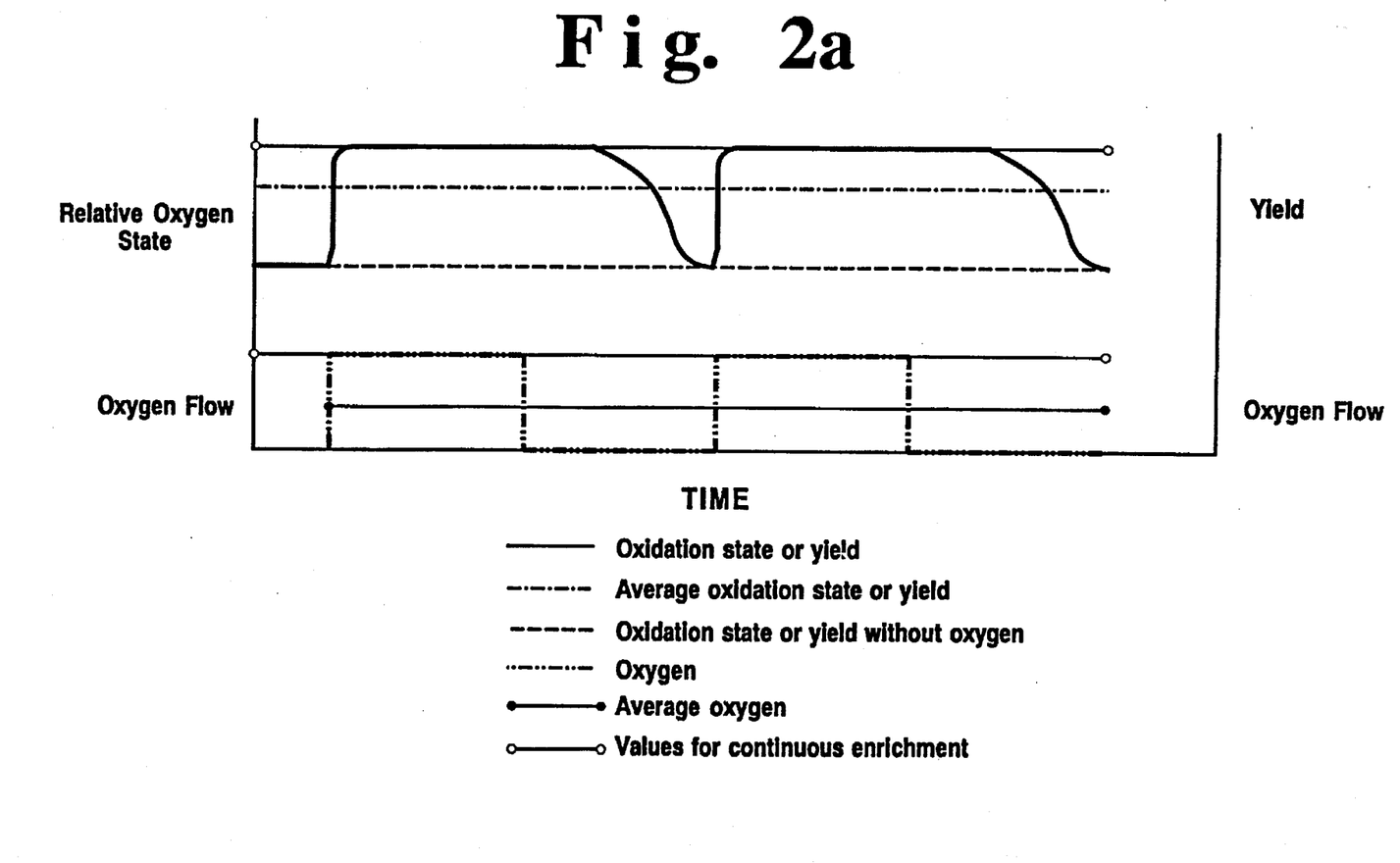
FIG. 2a is a graphical representation of a possible oxygen enrichment method of the invention. This method is compared with methods having continuous enrichment and no oxygen enrichment.

The first method is shown in FIG. 2a. In this figure the initial yield is that which is obtained in an air based reaction. A yield increase is obtained by adding oxygen to the reaction. After a maximum yield is attained, the oxygen continues to run for a short time, then turned off. By continuing to supply oxygen even after a maximum yield is attained, one is able to more completely reoxidize the catalyst in the system. As noted on the figure, the yield remains at an elevated level for a period after the oxygen is shut off. At this point the yield and oxidation states slowly return to their original values. Upon reaching this value, oxygen is again added and the cycle begins again. As can be seen the average yield may be increased due to the inventive process. When compared to FIG. 1, the disclosed example attains 70% of the yield benefit associated with a conventional oxygen enrichment process is obtained using only 50% of the oxygen required for that process.

It should be noted that the amount of time that the oxygen flow is maintained after a maximum yield is achieved is subject to optimization and design criteria. Clearly, if more or less oxygen use is desired then the oxygen may be cycled for longer or shorter periods of time with a concomitant effect upon average yield. In any event, the invention is based upon a recognition that a constant supply of oxygen is not required to maintain an elevated yield or oxidation state for the reasons set forth above.

Figure 2B:
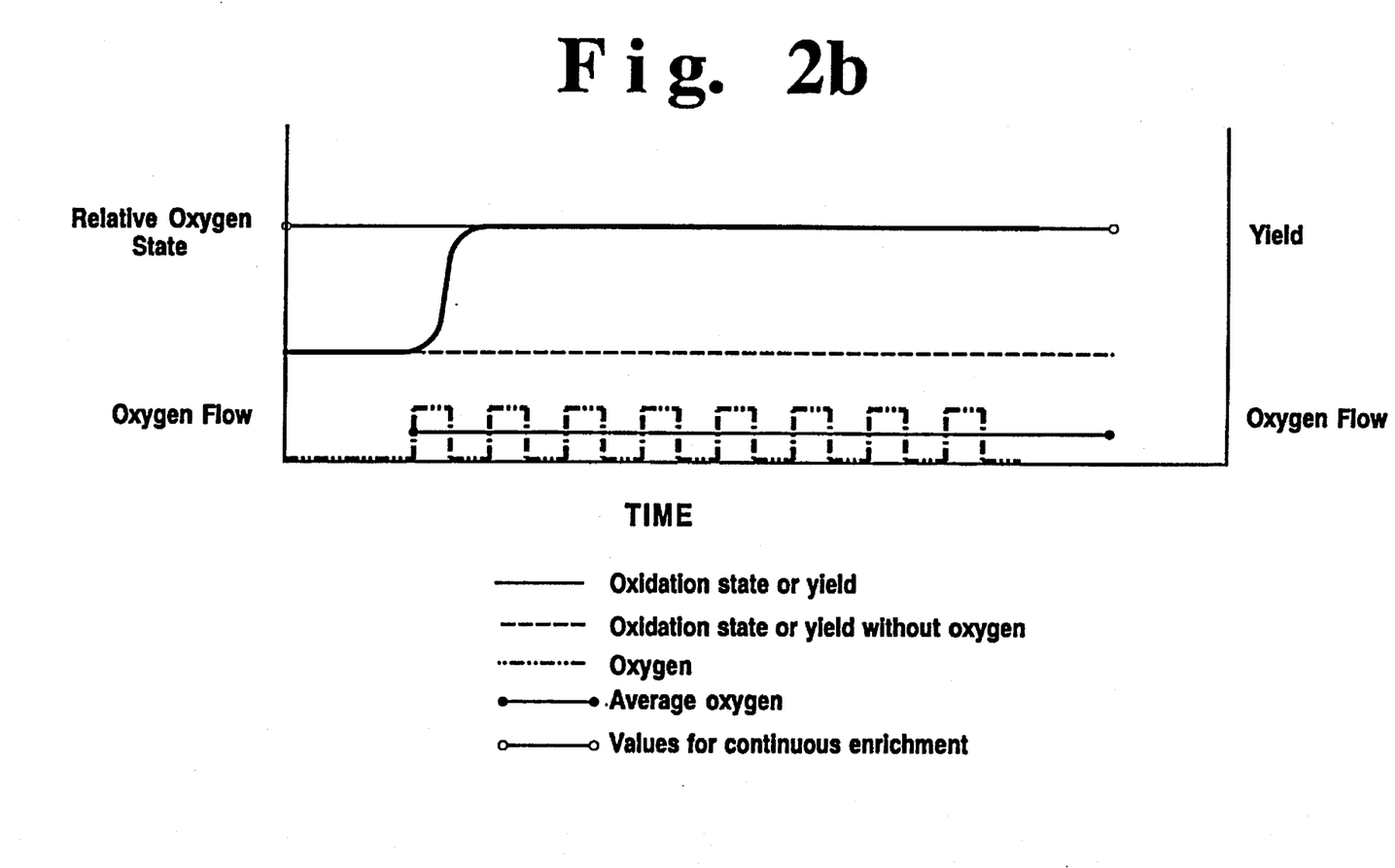
FIG. 2b is a graphical representation of a possible oxygen enrichment method of the invention. This method is compared with methods having continuous enrichment and no oxygen enrichment. In this figure the highest oxidation state or yield is the same as would be achieved under continuous enrichment.

A second alternative is illustrated in FIG. 2b. In this method, the increased yield is kept constant by regulating the oxygen supply such that oxygen is provided until a desired elevated yield is obtained, then is shut off. At a point immediately before the yield decreases, the oxygen is again turned on. In this way, the yield remains constant at 100% of what would have been achieved through continuous oxygen enrichment while using only 50% of the oxygen required in that process.

Note that in each of the above examples, air, reactant and catalyst feed are kept constant, while only the flow rate of oxygen is adjusted. This offers simplified operation over the conventional systems discussed previously.

There are seven variables to consider in the inventive process: location of oxygen injector site or sites, high oxygen flow rate, low oxygen flow rate, duration of the high oxygen flow rate regime, duration of low oxygen flow regime, and the profile of ramp-up from low flow rate to high flow rate, and ramp-down from high flow rate to low flow rate. These may be optimized depending upon the particular gas phase oxidation process used. What follows are some general considerations to take into account.

Figure 3A:
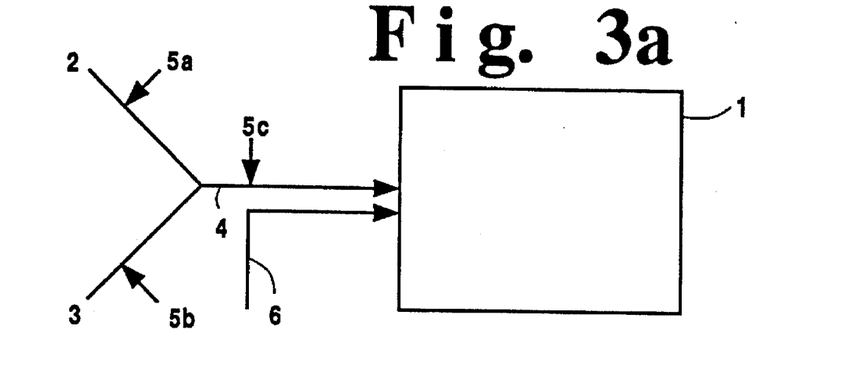
FIGS. 3a and 3b show alternative points at which oxygen may be inserted into the system for a fixed and fluid bed, respectively.
Figure 3B:
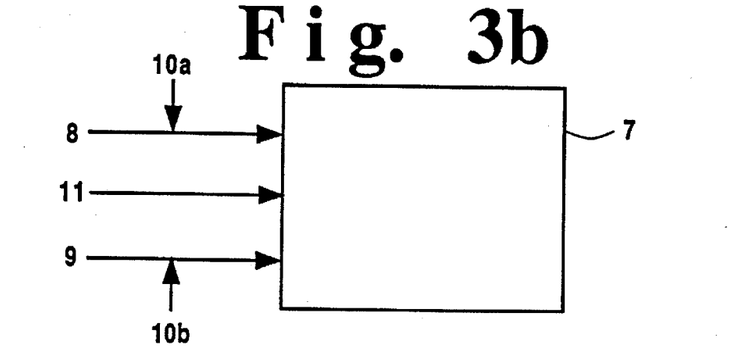

FIGS. 3a and 3b illustrate the possible alternatives for where oxygen may be injected into the process with respect to a fixed bed reactor 1 or fluidized bed reactor 7, respectively.

Figure 4A:
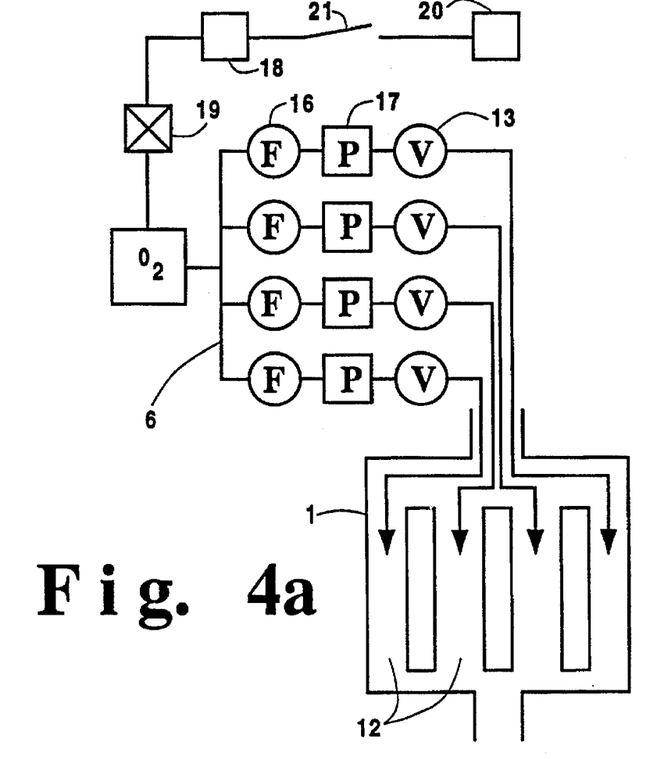
FIGS. 4a–4d and 5–7 show methods by which a continuous source of oxygen may be used to provide an alternating relatively high and relatively low flow of oxygen to the air based process of the invention.
Figure 4B:
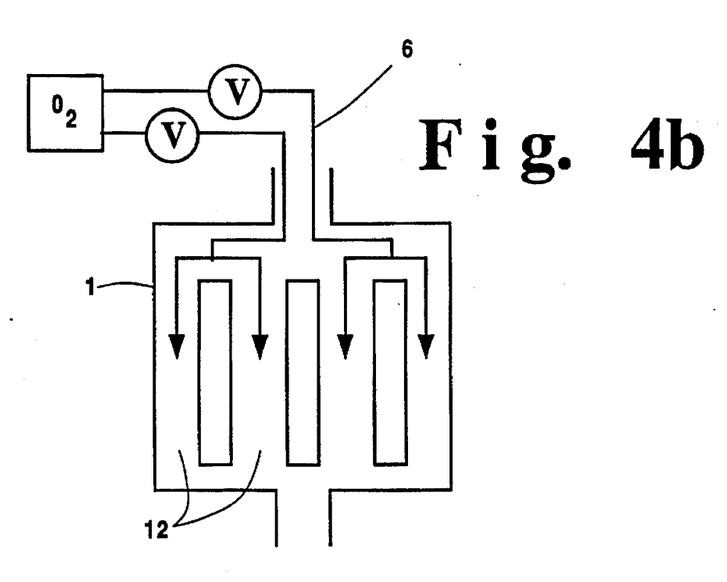

As is recognized in the art, and shown in FIG. 3a, a fixed bed reactor operates in such a manner that an air feed 2 and a reactant feed 3 are combined into a single mixture feed 4 outside the reactor. It is the mixture feed which passes into the reactor, the interior of which is shown in FIG. 4a.

Inside the reactor 1, this feed is passed through a plurality of tubes 12, each of which contain a redox catalyst, and wherein the reactant is oxidized to form product.

In the fixed bed process, oxygen may be injected into the air line 2 via line 5a, the reactant feed line 3 via line 5b, the combined air-feed mixture 4 via line 5c, or directly into the reactor 1 via manifold 6. Each of these locations are discussed below.

In fixed bed processes, since the feed and reactant are premixed, there is no difference in the effect of the oxygen whether it is injected into the air, the reactant or the mixed stream. From a safety and ease of operation perspective, injection into the air line 2 is preferred. It may also be desirable to inject the oxygen directly into the reactor via manifold 6. A more detailed explanation of the latter process may be understood with reference to FIGS. 4a–4d which show the interior of a fixed bed reactor.

As explained above, fixed bed reactors 1 are composed of many separate tubes 12 each filled with a redox catalyst. Therefore, an oxygen manifold 6 could be used to inject oxygen directly into the individual tubes as in FIG. 4a or into groups of tubes as in FIG. 4b. This manifold could also be used to cycle oxygen from one set of tubes to another through valves 13. Since these reactors contain a very large number of tubes (about 10,000), such a manifold would be complicated.

Figure 4C:
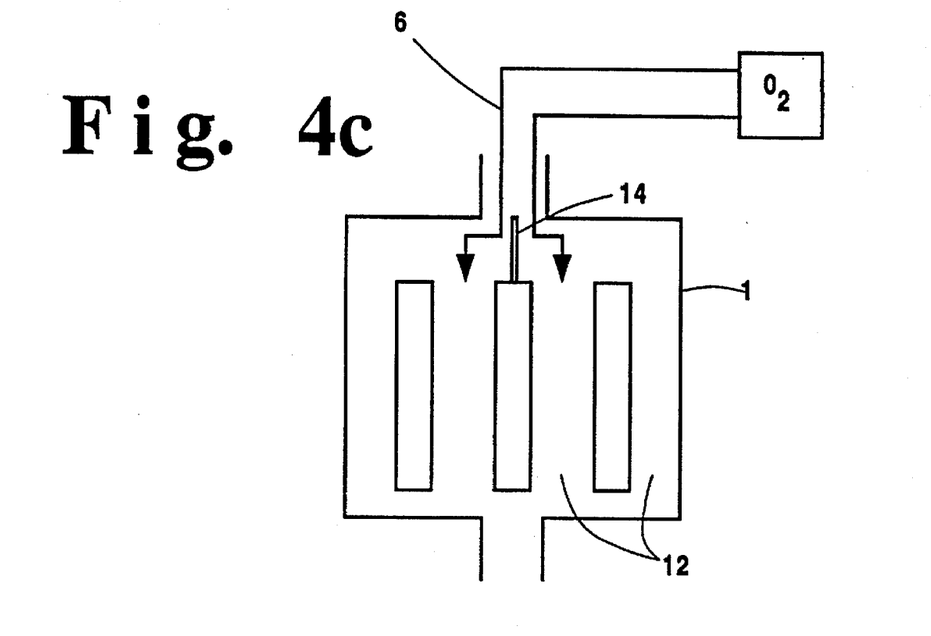

Another alternative is set forth in FIG. 4c, wherein a baffle 14 is used to section the reactor into groups of individual tubes 12, and manifold 6 is used to provide oxygen to each of these sections.

Figure 4D:
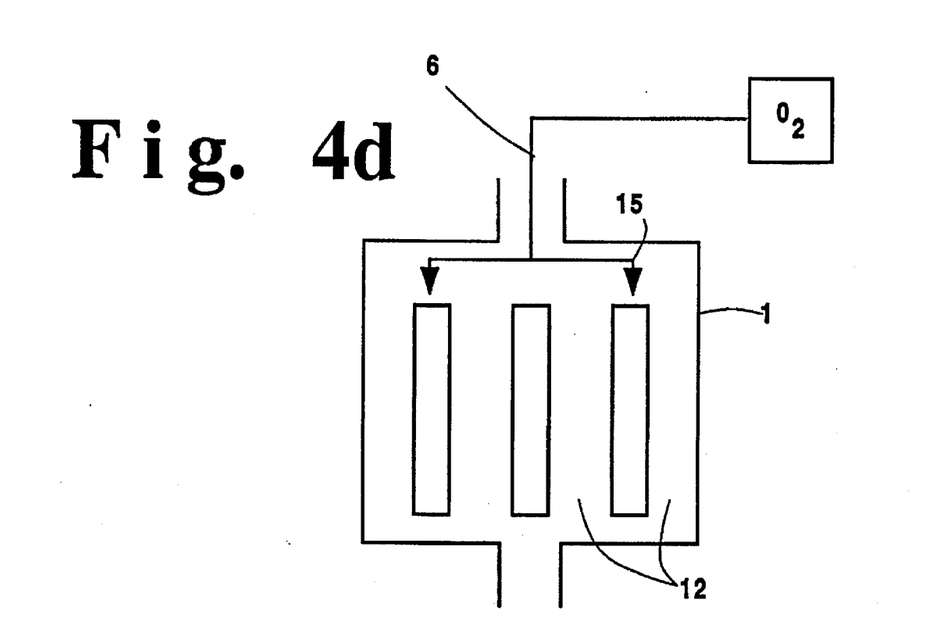

A final alternative is shown in FIG. 4d. In this alternative, oxygen flow is alternated between different regions of the reactor by injecting oxygen at different injector locations 15.

In any of the above embodiments set forth in FIGS. 4a–4d, the gas flow to each tube, groups of tubes or regions of the reactor may be controlled separately, as exemplified in FIG. 4a, through the use of flow meters 16, pressure gauges 17 and valves 13. The timing may be controlled by a timer 18 and solenoid valves 19. The timer and solenoid valves are supplied with power from a source 20 and are connected to that power source by a switch 21. One skilled in the art may run this system in a completely automated mode.

FIG. 3b shows the alternatives for injection of oxygen in a fluid bed reactor process. A fluid bed process differs from a fixed bed process, as shown in FIG. 3b, in that there is a separate air feed 8 and reactant feed 9 which pass directly into the reactor 7. There is no prior mixing of reactant and air. In a fluid bed process, catalyst circulates freely within the reactor.

Injection of oxygen into the air line 8 of a fluid bed via line 10a is simple, safe, and the generally preferred embodiment. However, there are advantages associated with injection of oxygen into the feed line 9 via line 10b or directly into the reactor via line 11 in the fluid bed alternative. Note that in this last option, oxygen may be injected into the reactor at different injector locations, in a similar fashion as was discussed above with respect to fixed-bed reactors.

Injection into the reactant feed line of a fluidized-bed reactor may minimize the oxygen requirement because oxygen is injected directly into a localized zone of over-reduced catalyst within the bed. This form of direct injection is disclosed in commonly assigned U.S. patent application Nos. 08/519,003 and 08/519,011, the contents of which are herein incorporated by reference.

However, injecting oxygen into the reactant feed line may increase the risk of feed and oxygen forming a dangerous flammable mixture within the oxygen piping. This could be avoided by providing a reduced flow of oxygen rather than turning off the oxygen altogether.

By injecting oxygen directly into the reactor via injector 11, one may be able to deliver the oxygen directly to the localized zone of over-reduced catalyst without incurring the safety concerns associated with injection into the reactant feed line. However, this requires adding an oxygen injector directly into the reactor, which is a costly operation.

As indicated above, oxygen flow rates are another factor which must be considered. The amount of oxygen injected into the reaction is determined by oxygen flow rates. In accordance with the invention, these rates are regulated at relatively high and relatively low levels. The higher the flow rate, the more oxygen is injected.

As indicated above, oxygen may be injected into several alternative locations in a reactor system. A similar flow rate results in a similar amount of oxygen added to the system, notwithstanding where in the system the oxygen is added.

In a preferred embodiment, oxygen is injected directly into the air feed line of a reactor. One may determine the volume percentage of oxygen in this combined air-oxygen mixture by adding the oxygen in air (21 vol. %) to the oxygen added, and dividing by the total volume of air plus oxygen. In a simple case, if 1.28 mole/hr of oxygen is added to a 100 mole/hr air stream, then there is (21+1.28)/(100+1.28) or 22 vol. % oxygen in the air feed. This amount of oxygen addition is typically referred to as 1% enrichment since the oxygen percentage is one percentage point greater than the amount of oxygen in the air stream.

However, this is not the volume % oxygen in the reactor, because in that case one must also take into account the amount of gaseous hydrocarbon reactant (HC) in the system. For example, in a fixed bed reactor a typical hydrocarbon volume % is 1–2% of the reaction atmosphere. Therefore, if the hydrocarbon percentage is 1% and the air flow is 100 mole/hr, the hydrocarbon flow will be 1.01 mole/hr (1.01/(1.01+100)=1 vol. percent. In order to determine the volume of oxygen percentage in the reactor when 1% oxygen enrichment is added the air feed, one must divide the volume of oxygen in enriched air stream by the volume of the enriched air stream plus the volume of the hydrocarbon stream. Therefore, if the standard hydrocarbon percentage without the addition of oxygen is one percent, and the hydrocarbon and air feeds are unaltered when the oxygen is added to the air stream there is (21+1.28)/(100+1.28+1.01) or 21.8 vol. % oxygen in the reactor. In this case, the oxygen concentration in the reactor is effectively diluted relative to the oxygen concentration in the air stream by the HC feed. It should be noted that in a fluidized bed reactor, reactant feed concentration, which includes ammonia in the ammoxidation reactions, ranges from 4% vol. % of the reaction atmosphere for maleic anhydride to 17 vol. % of the reaction atmosphere for acrylonitrile.

Again, it should be noted that the actual amount of oxygen added would be the same, notwithstanding the location, because the oxygen addition flow rate would be the same at each location. The oxygen vol. % differs only depending upon where in the system it is measured.

In terms of the amount of oxygen added, a preferred relatively low amount of oxygen is 0 vol. % (0% enrichment). However, the relatively low amount is limited only in that it must be less than the relatively high amount.

With respect to the relatively high amount, a preferred amount is 9 vol. % (9% enrichment) of the air feed or a resultant total of 29.5–29.7 vol. % oxygen in the reaction atmosphere of a fixed bed reactor assuming that there is no change in the original air and hydrocarbon flow rates (25.4–28.9 vol. % oxygen in a fluidized bed reactor). A more preferred amount is 1–3 vol. % (1–3% enrichment) of the air feed or a resultant total of 21.6–23.8 vol. % oxygen in the reaction atmosphere of a fixed bed reactor (18.3–23.1 vol. % oxygen in a fluidized bed reactor). However, the relatively high amount is limited only in that it must be greater than the relatively low amount.

While the above amounts of oxygen are generally applicable to all injection locations for fixed and fluid bed processes, certain considerations must be taken into account. For example, if injecting oxygen directly into the reactor, both high and low oxygen flow would be determined by process and safety considerations. If injecting oxygen into the reactant feed, the high oxygen flow would be limited by the upper flammability limit of the mixture so as to insure that the combined oxygen-feed mixture is not flammable. The low oxygen feed flow should be at least great enough so as to prevent the backstreaming of reactant feed into the oxygen piping.

As can be seen from FIGS. 2a and 2b, the cycle time may be in the range of seconds to days depending upon the particular oxidation reaction, catalyst, reactant and air feed rates. The exact cycle time is a function of optimization.

From an oxygen supply viewpoint, it is desirable to provide a continuous flow of oxygen rather than a fluctuating flow. However, if the consumption of oxygen is periodic as in the instant invention, significant amounts of oxygen will be vented and wasted if the oxygen supply is periodic. There are four methods by which a continuous flow of oxygen can be used to achieve fluctuating enrichment. These are, in order of preference, 1) direct flow from a single adsorption bed, 2) cycling between parallel reactor trains, 3) using an accumulator and 4) cycling within a single reactor.

Figure 5:
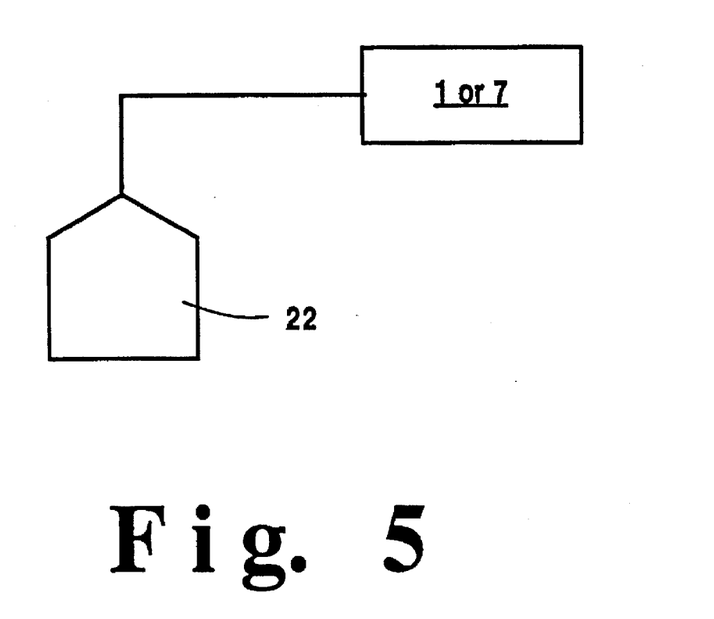

A single adsorption bed arrangement is shown in FIG. 5. A single adsorption bed 22 produces oxygen in a periodic way and is typically attached to an accumulator in order to produce a continuous flow. If the cycle time of the adsorption bed is the same as the cycle time required by the process, then the single adsorption bed could be coupled directly to the reactor 1 or 7 without using an accumulator.

Figure 6:
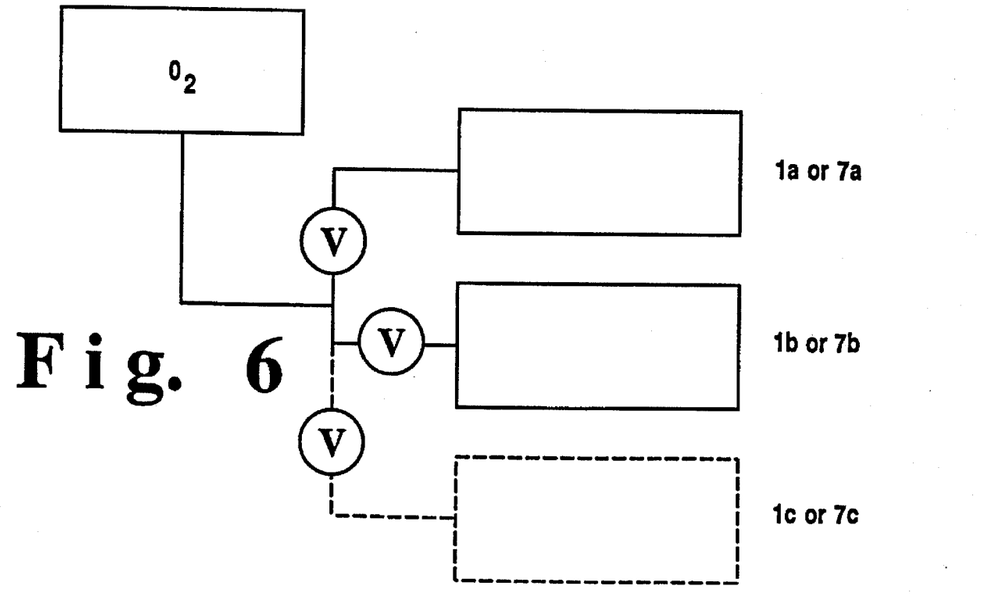

Chemical plants often employ multiple parallel reactor trains, as shown in FIG. 6. For the purposes of the instant invention, oxygen can be alternated between two or more reactors 1a or 7a, 1b or 7b and/or 1c or 7c in such a manner that while one or more, but not all of the reactors receive a flow of oxygen in a relatively high amount, the remaining reactor or reactors receive a flow of oxygen in a relatively low amount. Note that this embodiment is not available if the plant only employs a single reactor.

Figure 7:
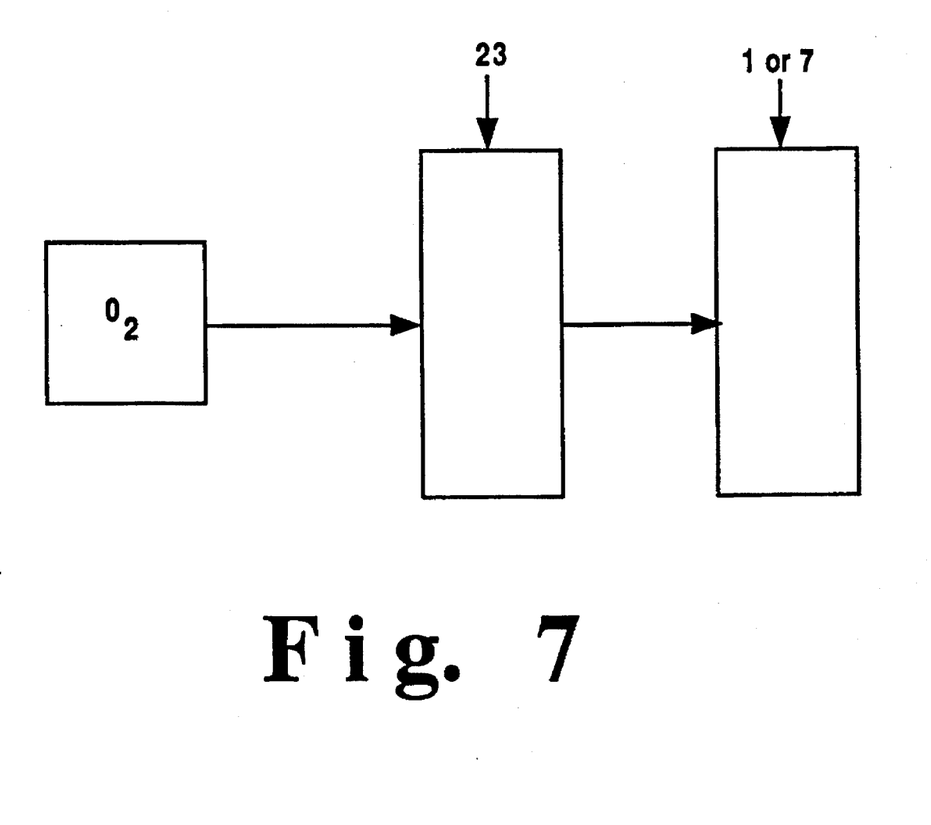

If the cycle time is on the order of one hour or less, an accumulator could be placed in the oxygen supply line as illustrated in FIG. 7. The oxygen supply source would continuously feed the accumulator 23, while the oxygen is periodically withdrawn to the reactor 1 or 7. This is similar to how a continuous flow is provided in a conventional adsorption bed set up. As implied above, this option is unavailable for cycle periods which are greater than on the order of one hour. This is because the required accumulator and compression equipment would simply be too expensive.

As discussed above, and shown in FIGS. 4a–4d fixed bed reactors are composed of many separate tubes 12 each filled with redox catalyst. An oxygen manifold could be used to inject oxygen directly into these tubes. The manifold could either inject oxygen individually into each tube or into a series of tubes via valves 13. The manifold would be used to cycle oxygen from one set of tubes to another within the reactor. Specifically, the fixed bed reactors would comprise at least two sets of tubes having catalyst therein, each set comprising one or more, but not all of said tubes, and wherein the oxygen flow to each set of tubes is regulated via a manifold such that a flow of oxygen is alternated between each set, and when oxygen is injected into a first set or sets in said relatively high amount, oxygen is injected into a second set or sets in said relatively low amount.

As suggested above, a baffle 14 could also be used in this capacity. Note that the manifold and baffle options are unavailable for fluid bed reactors, as they are not divided into individual sections. Further, the reactor head must be able to accommodate the manifold or baffle.

Also as suggested above, different injectors 15 could be used to inject oxygen into different regions of the reactor.

It should be noted that any of the above methods could be used to supply a gas to any manufacturing process where a fluctuating supply of that gas is desired.

Specific features of the invention are shown in one or more of the drawings for convenience only, as each feature may be combined with other features in accordance with the invention. Alternative embodiments will be recognized by those skilled in the art and are intended to be included within the scope of the claims.

What is claimed is:

1. In an improved process for the selective gas phase oxidation of an organic reactant using a metal oxide redox catalyst, wherein the organic reactant and air feeds are at a substantially continuous level, the improvement comprising adding oxygen to the gas phase in alternating relatively high and relatively low amounts.

2. The improved process of claim 1, wherein the oxidation takes place in a fixed-bed reactor or a fluidized-bed reactor.

3. The improved process of claim 1, wherein the relatively low amount of oxygen is greater than or equal to 0% enrichment, and is less than the relatively high amount.

4. The improved process of claim 1, wherein the relatively high amount of oxygen is less than or equal to 9% enrichment, and is greater than the relatively low amount.

5. The improved process of claim 3, wherein the relatively low amount of oxygen is 0% enrichment.

6. The improved process of claim 4, wherein the relatively high amount of oxygen is 1–3% enrichment, and is greater than the relatively low amount.

7. The improved process of claim 1, wherein the oxygen is added in such a manner so as to increase the average yield of said oxidation.

8. The improved process of claim 7, wherein said increased average yield is regulated by providing oxygen in the following manner:
   a) adding oxygen to the reaction such that a relatively high yield is attained;
   b) reducing said supply of oxygen until such a time immediately before said relatively high yield decreases;
   c) adding oxygen in such an amount to maintain said relatively high yield;
   d) repeating steps b and c so that said relatively high yield is maintained at a constant level.

9. The improved process of claim 7, wherein said increased average yield is regulated by providing oxygen in the following manner:
   a) adding oxygen to the reaction such that a relatively high yield is obtained;
   b) reducing said supply of oxygen until a relatively low yield is obtained;
   c) repeating steps a and b such that the average yield is greater than the relatively low yield.

10. The improved process of claim 2, wherein either said fixed-bed reactor or said fluidized bed reactor has an air feed and an organic reactant feed, and wherein oxygen is injected into the air feed.

11. The improved process of claim 2, wherein the reactor has an air feed and an organic reactant feed, and wherein oxygen is injected into the organic reactant feed.

12. The improved process of claim 2, wherein the reactor is a fixed bed reactor and wherein the reactor has a feed which comprises a mixture of air and organic reactant, and wherein oxygen is injected into this feed.

13. The improved process of claim 2, wherein the oxygen is injected directly into the reactor.

14. The improved process of claim 2, wherein the reactor is a fixed bed reactor comprising at least two sets of tubes having catalyst therein, each set comprising one or more, but not all of said tubes, and wherein the oxygen flow to each set of tubes is regulated via a manifold or baffle such that a flow of oxygen is alternated between each set, and when oxygen is injected into a first set or sets in said relatively high amount, oxygen is injected into a second set or sets in said relatively low amount.

15. The improved process of claim 2, wherein oxygen is injected into different regions within said fixed-bed or fluidized bed reactors.

16. The improved process of claim 1 wherein the oxidation takes place in a reactor system having two or more parallel reactors, and wherein the oxygen is alternated between reactors in such a manner that while one or more, but not all reactors receive oxygen in said relatively high enrichment amounts, the remaining reactor or reactors receive oxygen in said relatively low enrichment amounts.

17. The improved process of claim 1, wherein the oxygen is provided from a single adsorption bed which is directly attached to the reactor.

18. The improved process of claim 1, wherein the oxygen is provided from an accumulator.

* * * * *